US007206442B1

(12) United States Patent
Herod et al.

(10) Patent No.: US 7,206,442 B1
(45) Date of Patent: Apr. 17, 2007

(54) OPTICAL INSPECTION METHOD UTILIZING ULTRAVIOLET LIGHT

(75) Inventors: David W. Herod, Greenville, TX (US); Kathleen Hennessey, Richardson, TX (US); Youling Lin, Richardson, TX (US)

(73) Assignee: Rudolph Technologies, Inc., Flanders, NJ (US)

( * ) Notice: Subject to any disclaimer, the term of this patent is extended or adjusted under 35 U.S.C. 154(b) by 739 days.

(21) Appl. No.: 10/298,391

(22) Filed: Nov. 18, 2002

Related U.S. Application Data (60) Provisional application No. 60/332,479, filed on Nov. 16, 2001.

(51) Int. Cl.
*G06K 9/00* (2006.01)
*G01N 21/00* (2006.01)

(52) U.S. Cl. .................................... 382/141; 356/237.5

(58) Field of Classification Search ................ 382/145, 382/147, 149; 356/237.5
See application file for complete search history.

(56) References Cited

U.S. PATENT DOCUMENTS

| | | | | |
|---|---|---|---|---|
| 4,449,818 | A * | 5/1984 | Yamaguchi et al. | 356/237.3 |
| 5,502,466 | A * | 3/1996 | Kato et al. | 356/499 |
| 5,621,532 | A * | 4/1997 | Ooki et al. | 356/444 |
| 5,777,729 | A | 7/1998 | Aiyer et al. | |
| 6,246,788 | B1 * | 6/2001 | Pattikonda et al. | 382/147 |
| 6,335,531 | B1 * | 1/2002 | Somerville et al. | 250/459.1 |
| 2001/0012107 | A1 * | 8/2001 | Toh | 356/601 |
| 2001/0015410 | A1 * | 8/2001 | Imai et al. | 250/370.01 |

FOREIGN PATENT DOCUMENTS

JP    1061359    *    8/2000    .............. 382/145

OTHER PUBLICATIONS

The center for occupational research and development, LEOT Laser Tutorial, 1988, p. 8.*

* cited by examiner

*Primary Examiner*—Joseph Mancuso
*Assistant Examiner*—Hadi Akhavannik
(74) *Attorney, Agent, or Firm*—Slater & Matsil, L.L.P.

(57) ABSTRACT

A system and method for inspecting structures formed on the surface of an object using ultraviolet (UV) light. The object is placed in position and illuminated with at least one wavelength of UV light, directed at its surface from a UV source. At the moment of illumination, an image is captured by a UV-light sensitive camera positioned at an angle calculated to intercept light diffracted at particular an angle of diffraction associated with the pattern of structures formed on the surface of the object. To avoid having to repeatedly reposition the camera, one (or more in succession) illumination wavelength is selected to direct an intensity peak associated with a particular order of diffraction at the camera location. Ideally, a visible-light sensitive camera is also used to capture images of the surface when illumination with UV light results in the emanation of light in the visible portion of the spectrum.

16 Claims, 6 Drawing Sheets

OPTICAL INSPECTION METHOD UTILIZING ULTRAVIOLET LIGHT

RELATED APPLICATIONS AND CLAIMS OF PRIORITY

This patent application is related to and claims the benefit of the filing date of U.S. provisional patent application No. 60/332,479, filed Nov. 16, 2001.

BACKGROUND OF THE INVENTION

1. Technical Field of the Invention

This invention generally relates to the field of optical inspection, and more specifically to the automated or semi-automated optical inspection of regularly-patterned structures on production surfaces, such as those on semiconductor wafers, using ultraviolet (UV) light.

2. Description of Related Art

Optical inspection of articles of manufacture, either finished or in-process, may range from simple visual inspection to sophisticated computer-assisted inspection. Automated inspection is increasingly valuable as equipment and techniques improve because it is fast, reliable, and can frequently detect production defects that cannot be easily perceived by the unaided human eye.

This is true in the case of the in-process inspection of semiconductor wafers. Semiconductor wafers are manufactured in stages, with each stage representing the development of a new layer, or set of surface structures that form a functional part of the electronic devices that will populate the wafer when it is finished. The structures of each stage are formed by selectively etching away or treating carefully selected areas of the surface. The selection of areas to be etched or treated is often accomplished by covering the remaining area with a protective material called photoresist.

The photoresist is first applied evenly to the entire wafer surface, then selectively exposed to light emitted through a mask. This changes the nature of the exposed area so that it becomes, for example, more or less soluble. Then during development, the exposed areas are either retained or washed away (depending on the type of photoresist used), leaving a pattern of resist structures that will protect the wafer surface under them as the remainder of the surface is altered. During the process of etching, for example, unprotected areas are removed to a certain depth, perhaps to be filled later or otherwise treated. The protective photoresist is then removed, leaving only the desired surface configuration. The next stage can then be prepared for treatment and the process repeated until the desired surface structures have been completely formed.

Frequent inspections of the wafer surface are desirable during the production process, especially at the point where photoresist structures have been formed. Although many types of defects can be repaired, the photoresist is relatively easily removed and reapplied, so it is most advantageous to detect defects in it, rather than etching an improperly treated wafer that would be more difficult and expensive to repair.

Wafers in the process of manufacture can, of course, and sometimes are visually inspected for defects. Generally, however, an automated inspection system is used. In such systems, some form of electromagnetic energy, often but not always visible light, is directed at the surface to be inspected. The image created by the light reflecting from the surface is then captured and translated into digital form for processing by a computer.

The surface-image data may, for example, be analyzed to determine if unusual or tell-tale patterns are present that are commonly associated with certain kinds of defects. In one such technique, called image decomposition, surface structures are traced and described in terms of image grammars composed of units called primitives. One such technique is explained in detail in co-owned and co-pending U.S. patent application No. 09/074,301, entitled SYSTEM AND METHOD OF OPTICALLY INSPECTING MANUFACTURED DEVICES, filed May 6, 1998, a continuation-in-part of U.S. patent application No. 08/867,156, which issued on Jul. 18, 2000 as U.S. Pat. No. 6,091,846, entitled METHOD AND SYSTEM FOR ANOMALY DETECTION, both of which are incorporated herein by reference in their entirety. In some systems, the images associated with each inspection are classified, stored, and indexed for later use. Comparisons may be made to detect errors in the defect-detection process itself and to analyze the manufacturing process in order to determine, if possible, the root cause of frequently discovered defects in the hope of minimizing the occurrence of similar defects in the future.

In some instances, capturing an image of light reflected specularly from the wafer surface is inadequate for efficient and comprehensive defect detection. It has been found, for example, that defects such as focus offset (defocus errors) due to the presence of stray particles, errors in wafer development, etching or stripping, or to insufficient developer, are sometimes detectable by examining the light diffracted from the structures on the production surface. However, some defocus errors are so small as to require a high resolution imaging capability, and existing systems do not detect such errors.

When, as is the case with a properly-constructed semiconductor wafer, an object's surface features are small and sufficiently uniform so as to form a regular pattern that amounts to or approximates a diffraction (or, more properly, a reflection) grating, an analysis of the diffracted light is also useful. One method of using diffracted light is disclosed in U.S. Pat. No. 5,777,729 to Aiyer et al. Aiyer uses an elongated and extended monochromatic light source to illuminate an entire wafer surface, with each point thereon being illuminated by light at different angles. A diffraction efficiency is then calculated and utilized for defect detection. Other methods of using diffracted light are disclosed in co-owned and co-pending U.S. Provisional Patent Application No. 60/278,961 entitled, METHOD OF PERFORMING OPTICAL INSPECTION, filed Mar. 27, 2001, which is incorporated by reference herein in its entirety.

The utilization of diffracted light, however, somewhat complicates the inspection process. For example, when monochromatic light is directed at a known angle of incidence at a particular area on the wafer surface for which the grating pitch (i.e., distance between the regular surface features) is known, it is possible to predict the angle of first- (or other-) order diffraction, since the angle(s) of diffraction are a function of the grating pitch and the angle of incidence. For a light source in a fixed position, the camera or other image-capturing device used must be repositioned each time the grating pitch changes in order to capture light exiting the surface at a particular order of diffraction. Additionally, for a fixed light source and fixed grating pitch, the camera must be repositioned to capture light exiting the surface at different orders of diffraction. Finally, if the wavelength of the incident light is changed, once again, the camera must be repositioned to capture light exiting the surface at any particular order of diffraction.

In other words, to accommodate the varying surface patterns (i.e., grating pitches) commonly found on semiconductor wafers, to analyze different orders of diffraction for a fixed grating pitch, or to utilize light of varying wavelengths, either the camera or the light source must be relocated. This is due to the fact that each different grating pitch will yield a different angle of diffraction relative to the wavelength of the light and the angle of incidence. Of course, the orientation of the wafer could be adjusted according to the expected diffraction angle, but such adjustments are less than desirable because they are more cumbersome and introduce a greater risk of error.

Continuing advancement in semiconductor design and manufacturing is leading to smaller and smaller structures on the surface of the wafer. As structures on the wafer get smaller and smaller, a light source of shorter and shorter wavelengths is required to be able to resolve the structures and associated defects. Structure and defect sizes are now approaching the size at which the wavelengths in the visible light spectrum are too long to resolve the defects.

What is needed is a system and method that takes advantage of the ultraviolet light illumination during the automated inspection of objects such as semiconductor wafers, eliminates the need to make continual adjustments to the geometry of the inspection system, and utilizes a light source suitable for detecting extremely small structures and defects. The present invention provides such a system and method.

BRIEF DESCRIPTION OF THE DRAWINGS

The invention will be better understood and its numerous objects and advantages will become more apparent to those skilled in the art by reference to the following drawings, in conjunction with the accompanying specification, in which.

DETAILED DESCRIPTION OF EMBODIMENTS

FIGS. 1 through 7, discussed below, and the various embodiments used to describe the present invention are by way of illustration only, and should not be construed to limit the scope of the invention. Those skilled in the art will understand that the principles of the present invention may be implemented in any suitable device or system for the inspection of the surface of an object, in addition to the devices, systems, and applications specifically discussed herein.

Figure 1:
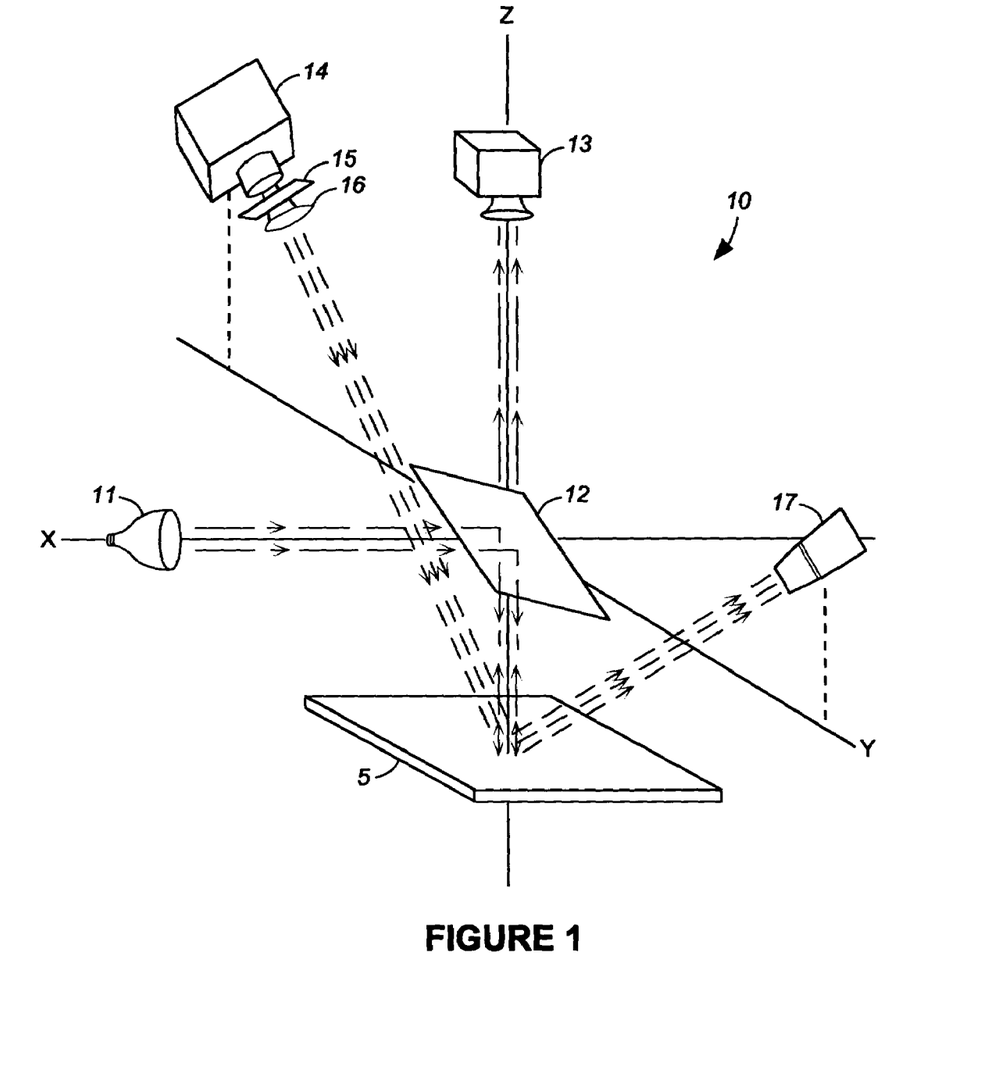
FIG. 1 is a perspective drawing of a preferred embodiment of the inspection system of the present invention.

FIG. 1 is a perspective drawing of a preferred embodiment of the inspection system 10 of the present invention. The components of the system 10 are mounted along perpendicular X-Y-Z axes. An object to be inspected such as a semiconductor wafer 5 is mounted on the Z-axis parallel to an X-Y plane. A diffuse visible light source 11 is mounted on the X-axis so that its light is directed along the X-axis to a 50/50 beam splitter 12 mounted at the X-Y-Z origin. The beam splitter is a semi-reflective surface mounted at a 45 degree angle to the X- and Z-axes. A portion of the visible light striking the beam splitter is reflected downward along the Z-axis where the light strikes the wafer normal to the surface. The beam splitter may be rotated about the Y-axis to direct reflected light to specific locations on the wafer surface. If the beam splitter is used to direct reflected light vertically downward onto the surface of the wafer 10, then the reflected light travels back up to the beam splitter where a portion of the light passes through the beam splitter and is captured by a visible light camera 13 mounted on the Z-axis.

An ultraviolet (UV) light source 14 is mounted in the Y-Z plane at a height sufficient to enable the UV light source to illuminate the surface of the wafer 10. A band pass filter 15 is mounted in front of the UV light source. The UV light source may be a broad bandwidth UV light source, and the band pass filter limits the range of wavelengths to a smaller desired band for the incident UV light. Several filters may be utilized, and the system may switch between the filters to select different narrow wavelength bands. A UV lens 16 is mounted in front of the light source and filter. The lens is used to control the illumination pattern on wafer 5, and in one embodiment may be used to collimate the dispersing light rays emitted by the UV light source and direct the collimated light onto the wafer surface. Since there is considerable absorption of UV light by glass, the lens is preferably constructed of a non-UV absorbing material.

A UV sensitive charged-couple device (CCD) camera 17 is also mounted in the Y-Z plane in a position to capture UV light emitted by the UV light source, and exiting from the surface of the wafer. The captured UV light may be light that is specularly reflected, or light that is diffracted at varying orders. The visible light illumination and the UV light illumination of the wafer surface may be performed simultaneously or sequentially.

Variables in the system configuration include the wavelength of the incident UV light, the angle of incidence, and the position of the UV camera 17 to capture either the reflected light or the diffracted light at different orders of diffraction. The UV light source 14 and UV camera 17 may be installed independently of the visible imaging components, and may be geometrically positioned so as to provide the greatest detection sensitivity. Once the wafer structure and geometry are known, the wavelength of the incident UV light can be shifted to compensate for diffraction order sensitivity. This enables the system, in essence, to steer the light exiting the wafer surface (either specularly or at different orders of diffraction) to the camera. This eliminates the requirement to physically reposition the camera to capture light exiting the surface when the grating pitch changes, or to capture light at different orders of diffraction.

Figure 5:
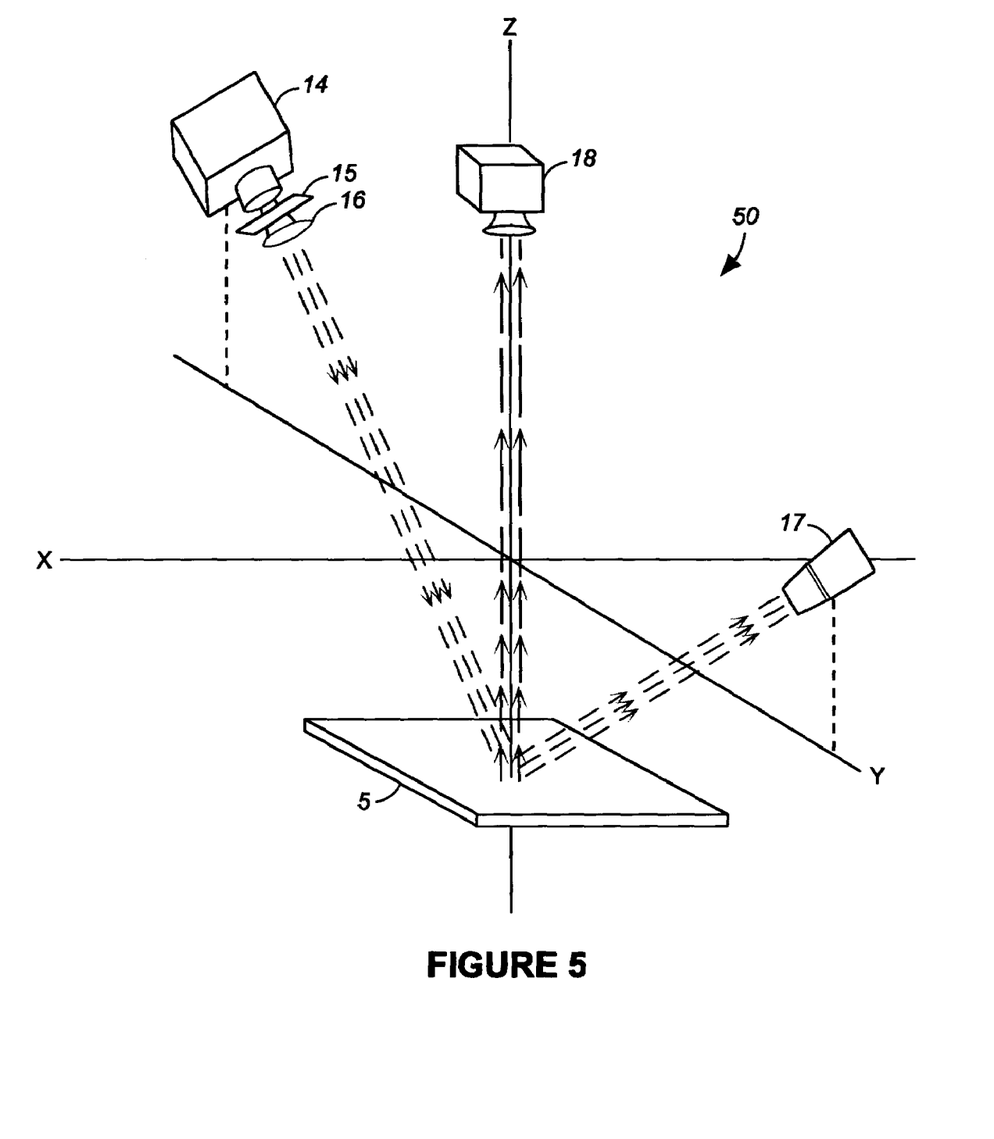
FIG. 5 is a perspective drawing of another preferred embodiment of the inspection system of the present invention.

FIG. 5 is a perspective drawing of another preferred embodiment of the inspection system of the present invention. In FIG. 5 it may be seen that the inspection system 50 is similar, though not identical to the inspection system 10 of FIG. 1. UV light source 14 is still mounted in the Y-Z plane so as to illuminate the surface of wafer 5. Band pass filter 15 and UV lens 16 are also present. The visible light source 11 of FIG. 1, however, is not used in the inspection system 50 of FIG. 5. For this reason, beam splitter 12 is also not required. In this embodiment, the wafer 5 will be illuminated solely by the UV source 14. It is noted, that if beam splitter 12 is designed to be movable (or removable) from its position in the configuration of system 10 (shown in FIG. 1), then that system may be used according to the description of inspection system 50 that follows.

Regarding the image capturing portion of the system, UV sensitive camera 17 is mounted as in inspection system 10 described above. Camera 18 may be a visible light camera (as is camera 13), but may alternately be able to detect infrared light or both visible and infrared. Note, however, that in this embodiment, while UV camera 17 must be mounted at an angle appropriate to capture a portion of the diffracted light (as described above), camera 18 may be mounted at a variety of positions. The direct overhead (Z axis) position for camera 18 (as shown in FIG. 5), however, remains the preferred embodiment.

The inspection system 50 shown in FIG. 5 takes advantage of a property of certain photoresist materials that are currently in use. These photoresist materials are specifically designed to be sensitive to illumination by light in the UV portion of the electromagnetic spectrum. In addition, the various patterned and unpatterned areas of the developed photoresist retain photosensitivity after development. That is, they absorb energy in the UV portion of the spectrum without further altering the chemical makeup of the photoresist deposition. These photoresist areas, in turn, re-emit the energy, but in the visible and possibly the infrared portion of spectrum. The energy shift associated with the difference between absorption and emission is called the "Stokes Shift", with the magnitude of the shift being a function of the particular photoresist used in the manufacturing process. The light emitted by the wafer 5 forms an image that can be captured by camera 18, which in this embodiment may employ filters to allow capture of (only) light in the visible or infrared portions of the spectrum. (Note that as used herein, the term "or" will include the sense sometimes expressed as "and/or".) If desired, the captured light may be further limited to only a portion of the visible or infrared spectrum.

Figure 6A:
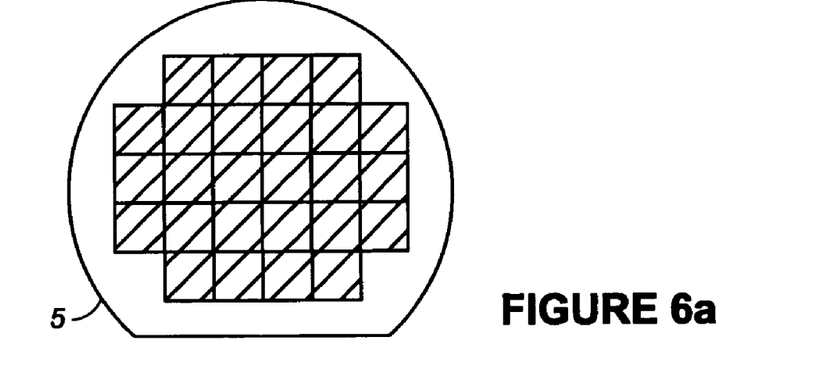
FIGS. 6a–6c are sketches of an exemplary semiconductor wafer as it may appear after illumination according to an embodiment of the present invention such as by the inspection system of FIG. 5.
Figure 6B:
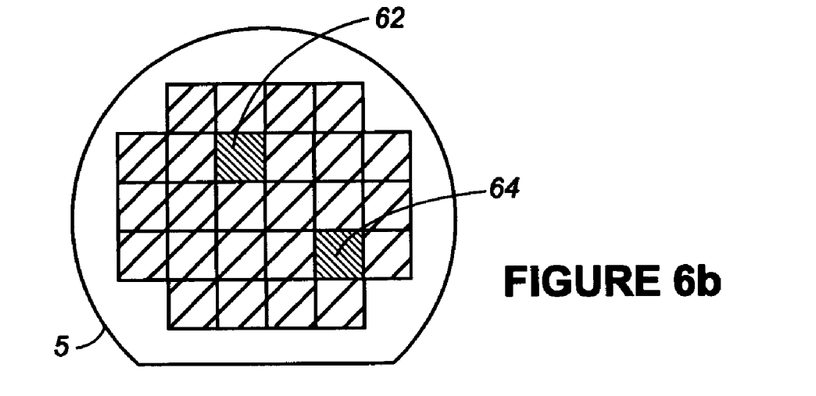
Figure 6C:
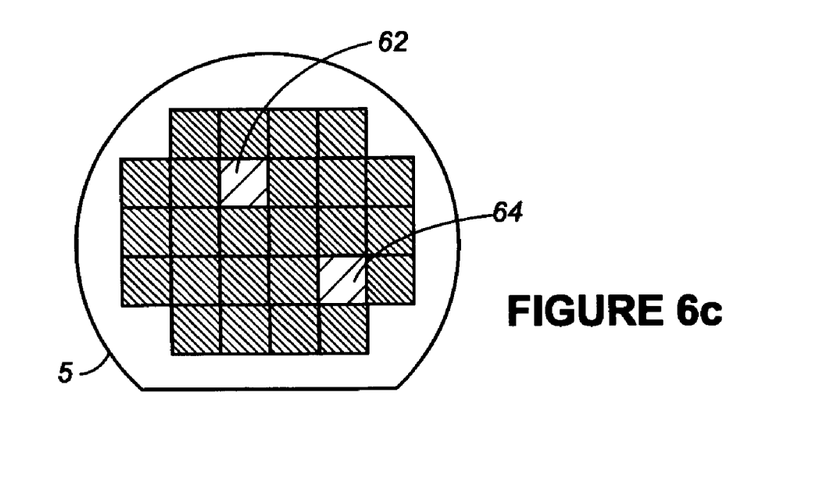

The image captured in this way by camera 18 may be used to highlight areas of the wafer 5 that have not been properly developed. FIGS. 6a–6c are sketches of an exemplary semiconductor wafer as it may appear after illumination according to an embodiment of the present invention such as by the inspection system of FIG. 5. Each "square" delineated on the exemplary wafer 5 in each of the figures represent a position of the stepper used during the development process, which exposes only a selected portion of the wafer at a time. In FIG. 6a, the wafer appears to be uniformly illuminated and therefore the image in this Figure shows no apparent defective areas. Note that certain wavelengths of ultra violent light may highlight the defects better than others. For this reason, several wavelengths (or portions) of the UV spectrum may be used serially to create a series of images that may be examined. In FIG. 6b, two of the areas 62 and 64 appear darker in contrast to the remaining areas of wafer on the surface of wafer 5. These are apparent defective sections that can then be marked for non-use, or repaired as is desired in the particular process being employed. In some embodiments, this result will be compared with differently-obtained results for confirmation that a defect does in fact exist before other measures are taken.

Note again that certain UV wavelengths will tend to highlight in greater contrast the borders between satisfactory and unsatisfactory portions or areas of photoresist deposition. In addition, additional wavelengths may produce images showing a similar but opposite result. In FIG. 6c, which is representative of an image captured after using a different UV wavelength (than was used to produce the image of FIG. 6a), the unsatisfactory portions of the semiconductor wafer surface appear as lighter than the satisfactory areas. For any particular design, the most advantageously-employed UV light wave length may be determined through a calibration or testing process using semiconductor wafers having known defects in specified areas.

As should be apparent, the defect highlighting technique described above may be advantageously used along with the diffraction effect method described in relation to FIGS. 1–4, where the use of identical equipment may be made, and where multiple wavelengths of UV light may also be required, or at least preferred. In addition, by using both methods to determine or attempt to locate defects, a higher degree of certainty in the effectiveness of the process may be achieved. In a particularly preferred embodiment of the present invention, both methods are used and the results compared to determine whether they are consistent, or whether a further evaluation of the particular semiconductor wafer will be needed to confirm the presence or absence of defects.

Of course, where configuration of the inspection system permits, an image captured while using a visible-light illumination source may still be used as well. Although these results may be compared with those achieved using UV light, however, use of the visible light source may impact detection of the image produced by re-emitted energy shifted from the ultraviolet to the visible portion of the spectrum, and so the visible light source may have to be used non-simultaneously. (It may be possible, of course, to use a single UV illumination event to produce the Stoke's-shift (visible or infrared) light image in camera 18 as well as the UV-light image in camera 17. In any event, the results obtained may be used, alone or in combination, to classify the defect or defects found according to various methods, such as those already known in the art.

Figure 7:
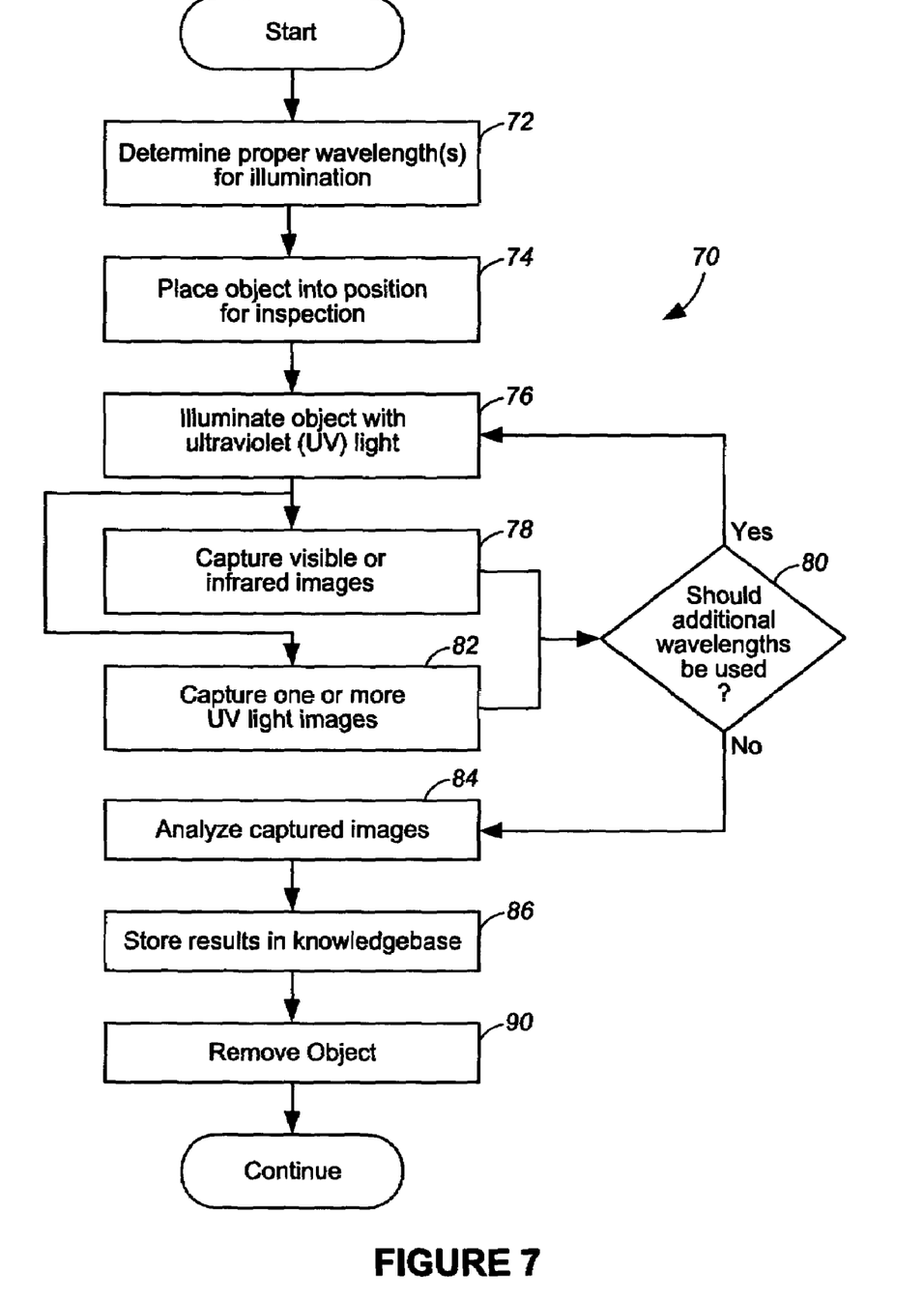
FIG. 7 is a flow chart illustrating a method of inspecting an object such as a semiconductor wafer according to an embodiment of the present invention.

FIG. 7 is a flow chart illustrating a method 70 according to one embodiment of the present invention. At start, it is presumed that an inspection system such as the inspection system 50 described in relation to FIG. 5 has been assembled and calibrated (to the extent necessary). At step 72, a series of test wafers are used in order to determine the most advantageous wavelengths for illumination. At step 74, a wafer (or other object) to be tested is placed into position. The wafer is then illuminated with UV light at a selected wavelength (step 76), and a visible-light image is captured (step 78). At decision block 80, the system determines whether additional UV wavelengths should also be used. If not, the process moves to analyzing the captured images (step 84) and adding the defect information collected to a defect knowledge base (step 86). If illumination with additional wavelengths is needed, the process returns to step 76 for additional illumination and image capturing (step 78). The process repeats itself as often as necessary for each desired illumination wavelength. At this point, the image captured using different wavelengths may be compared to confirm the presence or absence of defects (step not shown).

As alluded to above, a visible light test may also be conducted using a visible light source in connection with the visible-light capturing device (step not shown). A UV-light sensitive camera may also be present to capture light from the diffracted-light pattern as described above. This may be particularly useful in application where multiple-wavelength illumination sequences are performed. On the one-hand, certain wavelengths (or portions of the UV spectrum) will be optimum for showing contrast between satisfactory and unsatisfactory areas. On the other hand, certain wavelengths of UV light will (or should) produce a diffraction pattern that can be detected by the UV-light sensitive camera or cameras where they are oriented. As each successive illumination takes place, the images appropriate to each particular purpose may be captured. (Alternatively, unusable images may simply be discarded, or excluded from the analysis of step 84.) When all desired images have been captured, the wafer is removed from the inspection system (step 90). The process may then continue with the next wafer.

Figure 2:
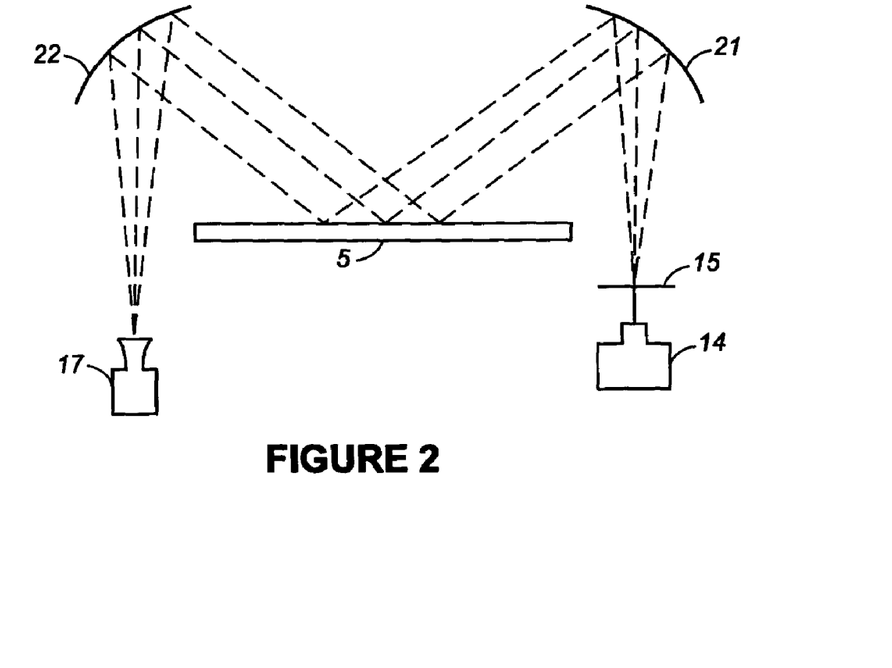
FIG. 2 illustrates an alternative method of illuminating a wafer surface with collimated light and detecting the effects thereof.

FIG. 2 illustrates an alternative method of illuminating a wafer surface with collimated light and detecting the effects thereof. Instead of using transmission optics (e.g., lens 16), parabolic mirrors 21 and 22 are utilized for both the illumination and camera optics. By using parabolic mirrors, the necessity of using non-UV absorbing is eliminated.

In this embodiment, the UV light source 14 produces diverging illumination that, after passing through the band pass filter 15, is reflected and collimated by the first parabolic mirror 21. The orientation of the first mirror directs the collimated light onto the surface of the wafer 10. Light that is reflected or diffracted off the surface of the wafer strikes the second parabolic mirror 22. The orientation of the second mirror focuses the light so that it can be captured by the UV camera 17. Once the wafer structure and geometry are known, the wavelength of the incident UV light can be shifted to compensate for diffraction order sensitivity. This enables the system, in essence, to steer the light exiting the wafer surface (either specularly or at different orders of diffraction) to the camera. This eliminates the necessity to move the camera to different positions when the grating pitch changes, or to capture the light at different orders of diffraction.

Figure 3:
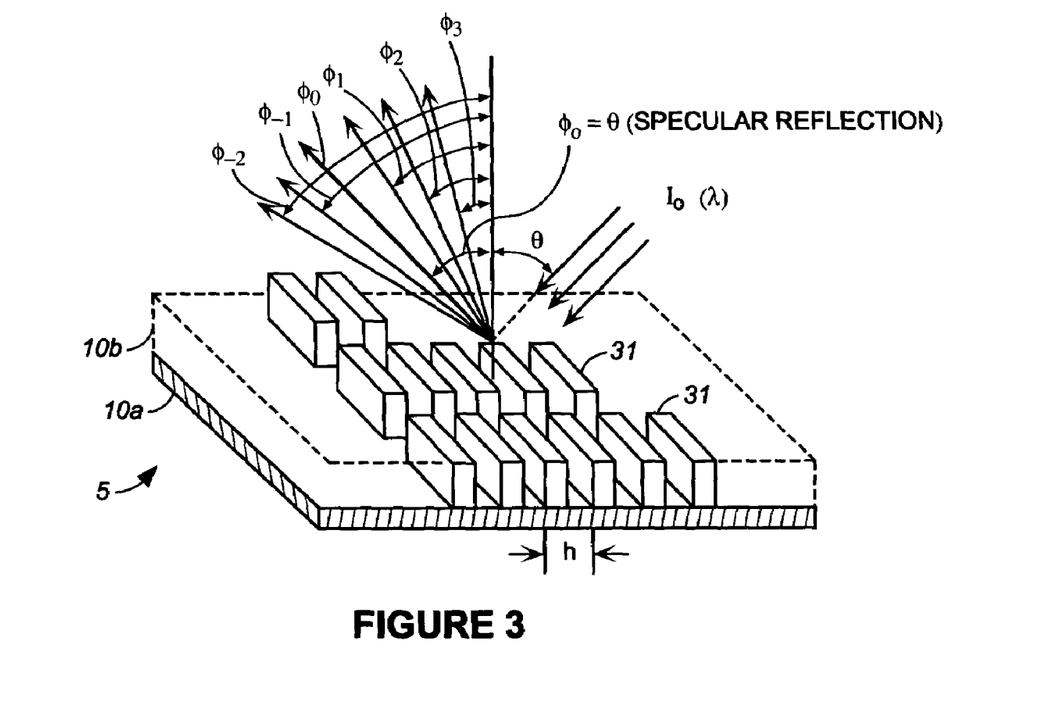
FIG. 3 is a perspective view of an exemplary wafer surface having a plurality of structures formed thereon that form a grating, which causes incident light to diffract.

FIG. 3 is a perspective view of the surface of a wafer 5 having a substrate 10*a* and a plurality of structures 31 formed on top of the substrate out of a photoresist layer 10*b*. The structures, which repeat with a pitch or separation parameter (h), form a grating structure which causes incident light to diffract. The separation parameter represents the pitch, or distance between the leading edge of a first structure on the surface, and the leading edge of an adjacent structure on the surface.

Diffracted light is generated by the pattern of structures that appears on the surface of the wafer. Light tends to diffract in bands, so there are several angles at which the diffracted light can be captured. Each band represents an order of diffraction.

Incident light with an intensity ($I_o$) arrives from the right at an angle of incidence $\Theta$. The incident arrows represent a wave front that illuminates the "textured" environment of the wafer, and is then diffracted. The diffracted components leave along different trajectories, dependent upon their "order" (n). The relationship between the wavelength of the light ($\lambda$), the separation parameter (h), the angle of incidence ($\Theta$), the order (n), and the exit angle of the diffracted wave front ($\Phi$) is given by the following equation:

$$h(\mathrm{Sin}\Theta - \mathrm{Sin}\Phi_n) = n\lambda$$

Note: both $\Theta$ and $\Phi$ are positive quantities, measured with respect to the surface perpendicular.

If the separation parameter (h), the angle of illumination ($\Sigma$), and the wavelength ($\lambda$), are fixed (i.e., made constant), the only remaining variables are the order of diffraction (n) and the exit angle of the diffracted wave front ($\Phi$) that is dependent upon the order (n).

The angle $\Phi$ is labeled as the difference between the normal axis and the exit angle of the diffracted wave front. The figure shows the incident light coming in at angle $\Theta$ and shows that for zero order diffraction (i.e., specular reflection), $\Phi_0 = \Theta$. Thus, the exit angle of the diffracted wave front for zero order diffraction is the same as specular reflection. Other orders of diffraction are represented by $\Phi_{-2}$, $\Phi_{-1}$, $\Phi_1$, $\Phi_2$, $\Phi_3$, and so on.

Figure 4:
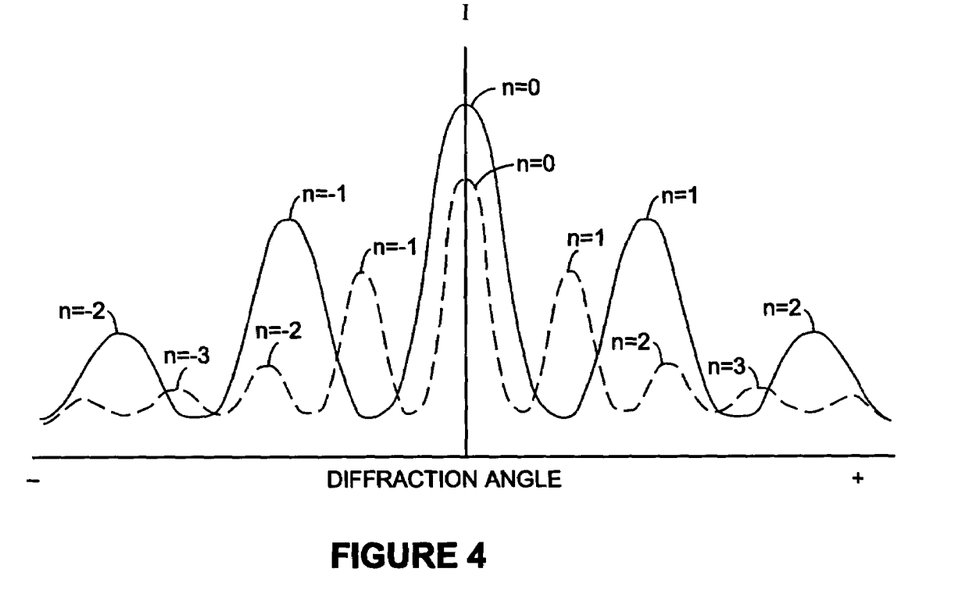
FIG. 4 illustrates a diffraction pattern associated with two different wavelengths of light that strike the wafer surface of FIG. 3.

FIG. 4 illustrates a diffraction pattern associated with two different wavelengths of light that strike the wafer surface of FIG. 3. Each of the peaks in the intensity distribution, represents a different order for that wavelength; each order of diffraction results in a peak intensity at its particular angle of diffraction. Note that although numerous orders are enumerated (e.g., "n=–2"), the actual number of discernable peaks may not be so limited. It should also be noted that the peaks for any given diffraction order do not occur at the same diffraction angle (i.e., the trajectory of the exiting radiation) for differing incident-illumination wavelengths. If a different wavelength is used, the diffraction pattern may (and probably will) change.

The presence of a diffraction pattern arising from the surface of a wafer indicates only that the surface has a grating (or grating-like) structure thereon; it does not indicate a defect in and of itself. As mentioned above, for a given grating structure, two different wavelengths of UV light will produce intensity spikes at different diffraction angles for a given order of diffraction. The difference in the diffraction angles is predictable. Therefore, if the difference between the diffraction angles differs from the predicted difference, then there is a likelihood that a defect exists in the structure, and due to the alteration in the light level detected by the camera, a contrast pattern will appear at the camera output.

The benefits of the present invention include increased sensitivity to defocus defects in the surface photoresist of deep UV-exposed wafers. The invention may also be useful for the detection of a broad range of varying wafer defects such as, for example, splits and discontinuities in the photoresist, close positioned double exposures, surface scratches, and underlying pattern errors. By varying the wavelength of the incident light, the exit angle of the diffracted light can be steered to the camera, eliminating the requirement to reposition the camera for each change of grating pitch or diffraction order. Finally, by utilizing a shorter wavelength in the UV spectrum for the incident light, an improvement in the resolution of closely spaced objects, imaged by the system, is provided. While other wafer inspection systems illuminate at wavelengths greater than 400 nm, this system utilizes illumination in the near UV, (i.e., 400 to 300 nm) and far UV (i.e., 300 to 200 nm), with a resulting improvement in image resolution and detection sensitivity.

It is thus believed that the operation and construction of the present invention will be apparent from the foregoing description. While the method, apparatus and system shown and described has been characterized as being preferred, it will be readily apparent that various changes and modifications could be made therein without departing from the scope of the invention.

We claim:

1. A method for inspecting structures formed on the surface of an object, the method comprising the steps of:
    placing the object into position for inspection, the surface of the object being oriented at an angle $\Theta$ relative to an ultraviolet (UV) light source and at an angle $\Phi$ relative to an image-capturing device;

determining at least a first UV wavelength corresponding to an expected diffraction wave front angle $\Phi_n$ equal to $\Phi$;

illuminating the object surface with UV light at the first determined wavelength and directed from the UV light source;

capturing at least one image formed by light emanating from the illuminated surface using the image-capturing device positioned at least one angle $\Phi_n$; and analyzing the at least one captured image to determine if defects exist in the formed structures.

2. The method according to claim 1, wherein the analysis is performed automatically.

3. The method according to claim 1, further comprising the step of classifying the defect determined to exist, if any, according to a pre-established system of classification.

4. The method according to claim 1, wherein the analysis includes comparing the actual diffraction pattern produced by the UV light reflecting off of the surface structures to an expected diffraction pattern.

5. The method according to claim 4, wherein the expected diffraction pattern is determined according to the formula $h(\sin\Theta - \sin\Phi_n) = n\lambda$.

6. The method according to claim 4, further comprising the steps of:

illuminating the object with UV light directed from a UV light source toward the surface at an angle $\Theta$ relative to the plane of the surface, wherein the UV light is at a second determined wavelength;

capturing at least one image formed by light emanating from the surface illuminated by the light of a second wavelength.

7. The method according to claim 6, wherein the diffraction pattern comparison includes comparing the patterns in images produced by UV light at different wavelengths.

8. The method according to claim 1, wherein the structures are formed in groups, the groups forming a discernable pattern in the object surface, and wherein the analysis includes comparing an image portion corresponding to at least one group with an image portion corresponding to at least one other group.

9. The method according to claim 1, further comprising illuminating the object surface with visible light from a visible light source.

10. The method of claim 9, wherein the structures are formed in groups, the groups forming a discernable pattern in the object surface, and wherein the analysis includes comparing an image portion corresponding to at least one group with an image portion corresponding to at least one other group.

11. The method according to claim 10, wherein the plurality of images used for comparison includes images produced by light from different portions of the UV spectrum.

12. A method for inspecting structures formed on the surface of an object, the method comprising the steps of:

placing the object into position for inspection, the surface of the object being oriented at an angle $\Theta$ relative to a UV light source and at an angle $\Phi$ relative to an image-capturing device;

determining at least a first UV wavelength corresponding to an expected diffraction wave front angle $\Phi_n$ equal to $\Phi$;

illuminating successive portions of the object surface with UV light directed from the UV light source at the first determined wavelength;

capturing a series of images using an image capturing device positioned at the at least one angle $\Phi_n$, each image captured while one of the successive surface portions are illuminated;

analyzing the at least one captured image to determine if defects exist in the formed structures.

13. The method according to claim 12, further comprising the step of repeating the illuminating and capturing steps using light from a second, different portion of the UV spectrum than the portion including the first wavelength.

14. The method according to claim 12, wherein the capturing step includes capturing images formed by visible or infrared light, wherein the visible or infrared light is produced by the UV light striking surface structures formed of a material that gives off visible or infrared light when illuminated with UV light.

15. The method according to claim 12, further comprising the steps of: illuminating at least a portion of the object surface with visible light; and capturing an image formed by the visible light reflecting from the surface.

16. A system for detecting defects in a pattern of surface structures formed on the surface of an object, said system comprising:

an ultraviolet (UV) light source for generating electromagnetic energy at a selected wavelength in the UV spectrum, wherein the UV source is positioned to direct at least a portion of the UV light toward the object's surface at a selected angle $\Theta$;

a UV-light sensitive image-capturing device positioned at an angle $\Phi$ relative to the surface;

means for determining at least a first UV wavelength corresponding to an expected diffraction wave front angle $\Phi_n$ equal to $\Phi$;

a non-UV-light sensitive image-capturing device for capturing an image produced by visible or infrared light emanating from the surface illuminated by UV light;

a database for storing the captured images; and a controller for analyzing the captured images to determine if a defect is present.

* * * * *